(12) United States Patent
Ruyra Baliarda et al.

(10) Patent No.: US 9,700,413 B2
(45) Date of Patent: Jul. 11, 2017

(54) APPARATUS AND METHOD FOR CHORDAL REPLACEMENT

(71) Applicant: Sorin Group Italia S.r.l., Milan (IT)

(72) Inventors: Xavier Ruyra Baliarda, Barcelona (ES); Monica Achiluzzi, Chivasso (IT); Laura Ghione, Turin (IT)

(73) Assignee: Sorin Group Italia, S.r.l., Milan (IT)

( * ) Notice: Subject to any disclaimer, the term of this patent is extended or adjusted under 35 U.S.C. 154(b) by 0 days.

(21) Appl. No.: 14/846,853

(22) Filed: Sep. 7, 2015

(65) Prior Publication Data

US 2015/0374495 A1    Dec. 31, 2015

Related U.S. Application Data

(63) Continuation of application No. 14/325,746, filed on Jul. 8, 2014, now Pat. No. 9,155,622, which is a continuation of application No. PCT/IT2013/000228, filed on Aug. 14, 2013.

(51) Int. Cl.
*A61F 2/24* (2006.01)

(52) U.S. Cl.
CPC .......... *A61F 2/2457* (2013.01); *A61F 2/2412* (2013.01); *A61F 2/2445* (2013.01); *A61F 2/2448* (2013.01); *A61F 2/2466* (2013.01)

(58) Field of Classification Search
CPC .... A61F 2/2442; A61F 2/2445; A61F 2/2448; A61F 2/2457
See application file for complete search history.

(56) References Cited

U.S. PATENT DOCUMENTS

| | | | |
|---|---|---|---|
| 3,656,185 A | 4/1972 | Carpentier |
| 4,055,861 A | 11/1977 | Carpentier et al. |
| 4,917,698 A | 4/1990 | Carpentier et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,084,151 A | 1/1992 | Vallana et al. |
| 5,104,407 A | 4/1992 | Lam et al. |
| 5,133,845 A | 7/1992 | Vallana et al. |

(Continued)

FOREIGN PATENT DOCUMENTS

| | | |
|---|---|---|
| CN | 1359279 A | 7/2002 |
| CN | 101460116 A | 6/2009 |

(Continued)

OTHER PUBLICATIONS

Bizzarri, Feederico et al., "Different ways to repair the mitral valve with artificial chordate: a systematic review", Journal of Cardiothoracic Surgery 2010, 5:22, 6 pages.

(Continued)

*Primary Examiner* — Jason-Dennis Stewart
(74) *Attorney, Agent, or Firm* — Faegre Baker Daniel LLP

(57) ABSTRACT

Described is a prosthetic device and methods for repairing a mitral valve having an annulus, leaflets, and chordae tendinae. The device comprises an elongate band including a plurality of reference elements that are located along the elongate band and protrude inwardly with respect thereto towards a center of the annulus, the plurality of reference elements being adapted to receive a corresponding plurality of artificial cords that are tied onto the reference elements and the plurality of reference elements adapted to be cut or removed in order to release the tied artificial cords.

12 Claims, 10 Drawing Sheets

(56) References Cited

U.S. PATENT DOCUMENTS

| | | |
|---|---|---|
| 5,370,684 A | 12/1994 | Vallana et al. |
| 5,387,247 A | 2/1995 | Vallana et al. |
| 5,423,886 A | 6/1995 | Arru et al. |
| 5,607,471 A | 3/1997 | Seguin et al. |
| 5,674,279 A | 10/1997 | Wright et al. |
| 5,716,397 A | 2/1998 | Myers |
| 5,824,066 A | 10/1998 | Gross |
| 5,873,812 A | 2/1999 | Ciana et al. |
| 6,102,945 A | 8/2000 | Campbell |
| 6,106,550 A | 8/2000 | Magovern et al. |
| 6,143,024 A | 11/2000 | Campbell et al. |
| 6,217,610 B1 | 4/2001 | Carpentier et al. |
| 6,250,308 B1 | 6/2001 | Cox |
| 6,309,414 B1 | 10/2001 | Rolando et al. |
| 6,406,493 B1 | 6/2002 | Tu et al. |
| 6,565,603 B2 | 5/2003 | Cox |
| 6,749,630 B2 | 6/2004 | McCarthy et al. |
| 6,797,001 B2 | 9/2004 | Mathis et al. |
| 7,220,227 B2 | 5/2007 | Sasaki et al. |
| 7,226,477 B2 | 6/2007 | Cox |
| 8,034,103 B2 | 10/2011 | Burriesci et al. |
| 8,216,303 B2 | 7/2012 | Navia |
| 2001/0021874 A1 | 9/2001 | Carpentier et al. |
| 2001/0039450 A1 | 11/2001 | Pavcnik et al. |
| 2002/0010504 A1 | 1/2002 | Alt |
| 2002/0188350 A1 | 12/2002 | Arru et al. |
| 2003/0083742 A1 | 5/2003 | Spence et al. |
| 2003/0108264 A1 | 6/2003 | Nishizawa et al. |
| 2003/0199974 A1 | 10/2003 | Lee et al. |
| 2003/0208264 A1 | 11/2003 | McCarthy et al. |
| 2003/0208284 A1 | 11/2003 | Stewart et al. |
| 2003/0220686 A1 | 11/2003 | Arru et al. |
| 2004/0039443 A1 | 2/2004 | Solem et al. |
| 2004/0249453 A1 | 12/2004 | Cartledge et al. |
| 2005/0004668 A1 | 1/2005 | Aklog et al. |
| 2006/0129227 A1 | 6/2006 | Hengelmolen |
| 2006/0149368 A1 | 7/2006 | Spence |
| 2006/0195183 A1 | 8/2006 | Navia et al. |
| 2006/0259135 A1 | 11/2006 | Navia et al. |
| 2007/0123979 A1 | 5/2007 | Perier et al. |
| 2007/0162112 A1 | 7/2007 | Burriesci et al. |
| 2007/0191940 A1 | 8/2007 | Arru et al. |
| 2009/0088837 A1 | 4/2009 | Gillinov et al. |
| 2009/0177266 A1 | 7/2009 | Powell et al. |
| 2010/0042147 A1 | 2/2010 | Janovsky et al. |
| 2010/0241222 A1 | 9/2010 | Ruyra Baliarda |
| 2011/0015727 A1 | 1/2011 | Ingle et al. |
| 2011/0118832 A1 | 5/2011 | Punjabi |
| 2013/0053951 A1 | 2/2013 | Ruyra Baliarda |
| 2015/0051698 A1 | 2/2015 | Ruyra Baliarda et al. |

FOREIGN PATENT DOCUMENTS

| | | |
|---|---|---|
| EP | 0338994 A1 | 10/1989 |
| EP | 1266641 B1 | 10/2004 |
| EP | 1348406 B1 | 12/2009 |
| EP | 2198806 A2 | 6/2010 |
| EP | 2548534 A1 | 1/2013 |
| SU | 577022 A1 | 10/1977 |
| WO | 9119465 A2 | 12/1991 |
| WO | WO2005072649 A1 | 8/2005 |
| WO | WO2005082278 A2 | 9/2005 |
| WO | WO2006089236 A1 | 8/2006 |
| WO | WO2006113906 A1 | 10/2006 |
| WO | WO2007072399 A1 | 6/2007 |
| WO | WO2009010619 A2 | 1/2009 |
| WO | WO2009133715 A1 | 11/2009 |
| WO | WO2009141665 A1 | 11/2009 |
| WO | 2011113986 A1 | 9/2011 |

OTHER PUBLICATIONS

Doi, Atsuo et al., "Intracardiac Calipers for Artificial Chordae Replacement in Mitral Valve Repair", The Annals of Thoracic Surgery, 2009, vol. 87, pp. 326-328.

Duran, Carlos M. et al., "Techniques for Ensuring the Correct Length of New Mitral Cords", The Journal of Heart Valve Disease, vol. 12, 2013, pp. 156-161.

European Search Report for EP 01830378.4, mailed Jan. 3, 2002, 3 pages.

European Search Report for EP 02425190.2, completed Apr. 8, 2003, 2 pages.

European Search Report for EP 05425926.2, mailed Jun. 27, 2006, 5 pages.

International Search Report and Written Opinion issued in PCT/ES2011/070183, mailed Jul. 29, 2011, 15 pages (with English transiations).

International Search Report and Written Opinion issued in PCT/IT2013/000228, mailed May 26, 2014, 12 pages.

Maisano, Francesco et al., "Transapical endovascular implantation of neochordae using a suction and suture device", European Journal of Cardio-thoracic Surgery, No. 36, 2009, pp. 118-123.

Maselli MD, Daniele et al., "A new method for artificial chordate length tuning in mitral valve repair: preliminary experience", The Journal of Thoracic and Cardiovascular Surgery, Aug. 2007, pp. 454-459.

Rankin MD, J. Scott et al., "Adjustable Artificial Chordal Replacement for Repair of Mitral Valve Prolapse", Ann Thorac Surg 2006, 81, pp. 1526-1528.

Ruyra-Baliarda, Xavier, "Preliminary experience with the no prolapsed system. A new device for ensuring the proper length of artificial chordate in mitral valve repair", Interactive CardioVascular and Thoracic Surgery, No. 10, 2010, pp. 165-167.

Supplemental European Search Report issued in EP Application No. 11755736, mailed Jun. 3, 2014, 5 pages.

International Preliminary Report on Patentability issued in PCT/IT2013/000228, mailed Feb. 16, 2016, 7 pages.

APPARATUS AND METHOD FOR CHORDAL REPLACEMENT

CROSS-REFERENCE TO RELATED APPLICATION

This application is a continuation of U.S. application Ser. No. 14/325,746, filed Jul. 8, 2014, which is a continuation of International Application No. PCT/IT2013/000228, filed Aug. 14, 2013, which is herein incorporated by reference in its entirety.

TECHNICAL FIELD

The present invention relates to devices and methods for repair of heart valves. More specifically, the invention relates to devices and methods for repairing mitral valve prolapse by replacement of chordae tendineae.

BACKGROUND

The mitral valve is one of the four valves of the heart having a complex structure. Various elements in the valve must function in a coordinated manner to cause blood to flow through the valve in an appropriate fashion. The mitral valve consists of two leaflets (anterior and posterior) that are attached to a fibrous ring (i.e., the annulus). The leaflets are anchored to papillary muscles in the wall of the left ventricle by a number of chordae tendineae (see, e.g., FIG. 1). As shown in FIGS. 1 and 2, a normal mitral valve annulus 10 has a posterior region and an anterior region situated between two trigones, which are fibrous structures that form part of the base of the heart. Under normal conditions, during the contraction phase of the heart (i.e., systole), the two leaflets come together (i.e., coapt) and close the valve, which inhibits blood flow from the ventricle into the aorta (i.e., regurgitation). The coaptation of the valve leaflets typically occurs at (or near) the level of the fibrous ring, in part due to the chordae tendineae which restrict the leaflets from rising above that level.

In mitral insufficiency of a degenerative origin, closure of the valve is insufficient because one of the leaflets (or both) moves above the plane of the annulus at least partially into the left atrium, causing what is commonly referred to as prolapse of the leaflets. One cause of prolapse is elongation or rupturing of one or more of the native chordae tendineae. One common technique for prolapse repair consists of use of artificial cords (i.e., "neocords"), often made of polytetrafluoroethylene (PTFE), to replace defective native chordae tendineae. These neocords are connected between the papillary muscles and a free edge of the leaflets and thus perform the function of the native chordae tendineae.

In mitral insufficiency, the valve annulus is often also dilated. In cases of severe mitral insufficiency, the patient often must undergo intervention to repair the valve or to replace the valve with an artificial valve prosthesis. A valve repair procedure typically has one or more of the following objectives: to restore the mobility of the leaflets without restriction or excess movement, to create an adequate coaptation surface or closure, and to remodel the shape and size of the dilated mitral annulus.

SUMMARY

According to various embodiments, the present invention provides a device and method that addresses two significant challenges associated with implanting neocords, namely determining the length required for optimal functionality and attaching the neocords to the native valve leaflets. According to some embodiments, the present invention is an annuloplasty device or an annuloplasty delivery device, which includes a plurality of reference elements, either separate or on a removable strip attached to the device, for the fixation of neocords thereto. The reference elements extend within the lumen of the annuloplasty device or on the delivery device such that they are capable of receiving such neocords. These reference elements serve to establish the proper length of the neocords that are to be attached to mitral valve leaflets. This neocord length sizing criteria is based on the well established clinical concept that the length of the artificial chords is similar to the distance between the tip of the papillary muscle and the annulus plane level.

Advantageously, the device allows the proper length of the neocords to be established during an operation for the repair of a prolapse of the mitral valve. No pre-measurement of the implanted neocords, or use of a tool to pre-measure, is required. The invention makes it possible to have reliable and reproducible results in determining the length of the neocords. Furthermore, the reference element function to prevent knots used to attach the neocords to the native leaflets from slipping. The reference elements are then removed or cut away, leaving the knots in place.

The present invention, according to Embodiment 1, is a prosthetic device for repairing a mitral valve having an annulus, leaflets, and chordae tendineae. The device comprises an elongate band including a plurality of reference elements that are located along the elongate band and protrude inwardly with respect thereto towards a center of the annulus. The plurality of reference elements are separated from each other and adapted to receive a corresponding plurality of artificial cords that are tied onto the reference elements. The reference elements are adapted to be cut to release the tied artificial cords.

Embodiment 2 is the prosthetic device of Embodiment 1 wherein each of the reference elements is formed by a suture that is fixed to the elongate band.

Embodiment 3 is the prosthetic device of either Embodiment 1 or Embodiment 2 wherein the elongate band is made of a flexible material.

Embodiment 4 is the prosthetic device of any of Embodiments 1-3 wherein the elongate band is arcuate in shape and has two free ends that are separated by an opening.

Embodiment 5 is the prosthetic device of any of Embodiments 1-4 wherein the elongate band is a closed ring.

Embodiment 6 is the prosthetic device of any of Embodiments 1-5 wherein the elongate band comprises a central core of a silicone material and an exterior covering of a polyester material.

Embodiment 7 is the prosthetic device of any of Embodiments 1-6 wherein the reference elements include one needle-passing lumen.

The present invention, according to Embodiment 8, is a prosthetic device for repairing a mitral valve having an annulus, leaflets, and chordae tendineae. The device comprises an elongate band including a removable strip, including a plurality of reference elements joined to the elongate band. The plurality of reference elements protrude inwardly with respect thereto towards a center of the annulus and are adapted to receive a corresponding plurality of artificial cords that are tied onto the plurality of reference elements. The reference elements are adapted to be cut or removed in order to release the tied artificial cords.

Embodiment 9 is the prosthetic device of Embodiment 8 wherein the elongate band is made of a flexible material.

Embodiment 10 is the prosthetic device of either of Embodiments 8-9 wherein the elongate band comprises a central core of a silicone material and an exterior covering of a polyester material.

Embodiment 11 is the prosthetic device of any of Embodiments 8-10 wherein the elongate band is arcuate in shape and has two free ends that are separated by an opening.

Embodiment 12 is the prosthetic device of any of Embodiments 8-11 wherein the elongate band is a closed ring.

Embodiment 13 is the prosthetic device of any of Embodiments 8-12 wherein the reference elements include one needle-passing lumen.

The present invention, according to Embodiment 14, is a device for repairing a mitral valve annulus. The device comprises an annuloplasty retaining member including a plurality of reference elements adapted to receive a corresponding plurality of artificial cords that are tied onto the reference elements. The reference elements are adapted to be cut or removed in order to release the tied artificial cords. An elongate handle is connected to the holding member for delivery of the annuloplasty device to the mitral valve annulus.

Embodiment 15 is the device of Embodiment 14 wherein the plurality of reference elements are located on a removable strip that is attached to the annuloplasty retaining member.

Embodiment 16 is the device of either of Embodiments 14-15 further comprising an annuloplasty device that is connected by sutures to the annuloplasty retaining member.

Embodiment 17 is the device of any of Embodiments 14-16 wherein the annuloplasty device is for repairing a mitral valve having an annulus, leaflets, and chordae tendinae, the device comprising an elongate band.

Embodiment 18 is the device of any of Embodiments 14-17 wherein the elongate band is made of a flexible material.

Embodiment 19 is the device of any of Embodiments 14-18 wherein the elongate band is arcuate in shape and has two free ends that are separated by an opening.

Embodiment 20 is the prosthetic device of any of Embodiments 14-19 wherein the elongate band is a closed ring.

While multiple embodiments are disclosed, still other embodiments of the invention will become apparent to those skilled in the art from the following detailed description, which shows and describes illustrative embodiments of the invention. Accordingly, the drawings and detailed description are to be regarded as illustrative in nature and not restrictive.

Figure 1:
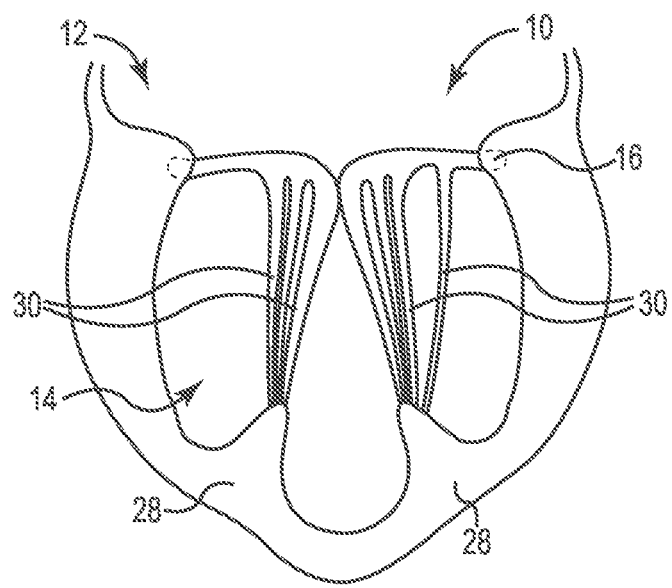
FIG. 1 is a schematic, sectional view of a portion of a heart including a mitral valve.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In the following description, numerous specific details are given to provide a thorough understanding of various embodiments. The embodiments can be practiced without one or more of the specific details, or with other methods, components, or materials. In other instances, well-known structures, materials, or operations are not shown or described in detail to avoid obscuring aspects of the embodiments. Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

FIG. 1 shows a schematic, sectional view of a portion of the heart including a mitral valve 10. As shown, the mitral valve 10 is generally located between the left atrium 12 and the left ventricle 14.

Figure 2:
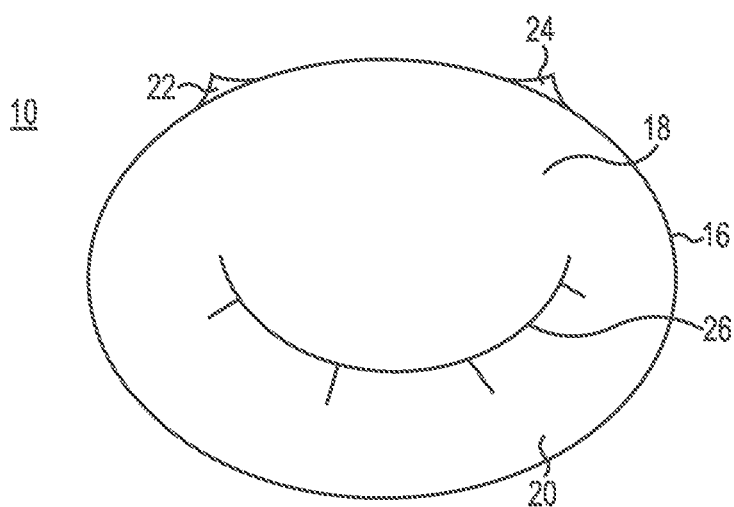
FIG. 2 is a schematic view of a mitral valve with two leaflets.

FIG. 2 shows a schematic top plan view of a mitral valve 10. As shown in FIGS. 1 and 2, the mitral valve 10 includes an annulus 16 and two leaflets, which are an anterior leaflet 18 and a posterior leaflet 20. The anterior leaflet 18 is typically coupled to the annulus 16 at least in part at the location disposed between the left fibrous trigone (LFT) 22 and the right fibrous trigone (RFT) 24. As shown, in a properly functioning heart valve the free edges of the anterior leaflet 18 and the posterior leaflet 20 generally come together and coapt during systole to form a coaptation zone 26. The leaflets 18, 20 are also attached to papillary muscles 28 in the left ventricle 14 by multiple chordae tendineae 30.

Figure 3:
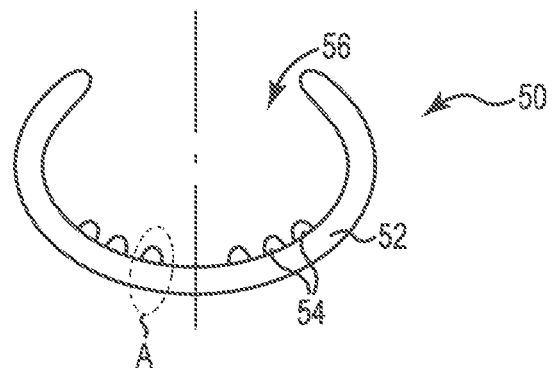
FIG. 3 is a plan view of a prosthetic device according to an embodiment of the invention.

FIG. 3 shows a prosthetic device 50, according to exemplary embodiments of the invention. According to various embodiments, the prosthetic device 50 is an annuloplasty device designed for the repair of a mitral valve annulus. As shown, the prosthetic device 50 has an open configuration and is generally shaped, for example, like a letter "C." According to other embodiments, the annuloplasty device has a closed configuration and is generally shaped, for example, like a letter "O" or a letter "D." According to various embodiments, the size and shape of prosthetic device 50 are selected to generally match the configuration of a patient's mitral valve annulus.

In various embodiments, the prosthetic device 50 includes an elongate element 52 including reference elements 54. Although other configurations are contemplated, the elongate element 52 may comprise a central core, and an exterior covering (not shown). The central core can be made of a material that is suitable for a desired stiffness. The central core may comprise a rigid, semi-rigid or flexible material, or may be a combination of rigid, semi-rigid, and/or flexible materials and/or portions. The central core preferably may comprise (e.g., consist essentially of) a molded polymeric element. One exemplary material for the central core is a silicone material, which is flexible. According to exemplary embodiments, the core may be formed of one or more of the tubular members disclosed in U.S. Pat. No. 8,034,103, which is hereby incorporated by reference in its entirety.

One exemplary material for the exterior covering is a polyester material. The exterior covering may comprise a knitted polyester (e.g., Dacron™) fabric, although woven, nonwoven (e.g., spun-bond, melt-blown, staple fiber matrix, etc.) or braided fabrics are also contemplated. The exterior covering may optionally be provided with any of various biocompatible coatings. According to exemplary embodiments, the coating may be any of the various coatings disclosed in U.S. Pat. No. 5,423,886, which is hereby incorporated by reference in its entirety.

The elongate element 52, according to various embodiments, may have any of a variety of cross-sectional shapes, including for example a generally circular cross-sectional configuration. According to other embodiments, the cross-sectional shape may be one or more of square, circular, rectangular, elliptical, triangular, or other similar shapes. Different cross-sectional shapes can be used to impart varying degrees of bending or torsional stiffness depending on the bending/twisting plane with respect to a section modulus. Also, according to some embodiments, the cross-sectional shape at different locations around the circumference of the elongate element 52 varies.

The prosthetic device 50 preferably has a low profile (e.g., cross-sectional thickness of about 3 mm). With this preferred low profile, the device 50 may reduce the potential for stenosis and turbulence within the valve, as well as onset of thrombus by minimizing the restriction or disturbance of blood flow through the valve.

Exemplary dimensions of the elongate element 52 may include a length of approximately 63 mm, which fits most adult patients. However, other lengths of elongate element 52 are also contemplated. According to some embodiments, a variety of sizes of elongate bands 52 having a variety of different length are packaged together such that a surgeon may select a prosthetic device 50 best suited for a particular patient.

As shown in FIG. 3, one or more reference elements 54 are located on or attached to elongate element 52. The reference elements 54 are separated from each other and protrude radially inward from the elongate band 54 towards an inner lumen 56. In some embodiments, the reference elements protrude radially inward in the same (or about the same) plane as the upper surface of the prosthetic device 50. In other embodiments, the reference elements protrude radially inward in the same (or about the same) plane as the lower surface (i.e., the surface in contact with the annulus) of the prosthetic device 50. In various embodiments, the reference elements 54 extend or protrude radially inward into the inner lumen 56, such that the reference elements are accessible by a suture needle (or other surgical instrument) during the mitral valve repair procedure.

Figure 4:
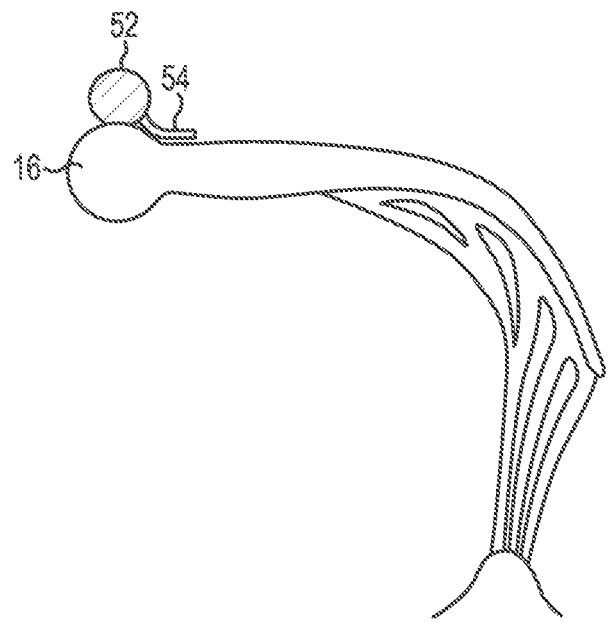
FIG. 4 is a schematic, cross-sectional view of a portion of a native mitral valve and annulus in which a prosthetic device is located according to an embodiment of the invention.

According to various embodiments, the reference elements 54 are configured to receive and couple with artificial chordae tendineae (i.e., neocords). In various embodiments, the reference elements 54 are sized and shaped to allow neocords to be individually knotted or tied to the reference elements 54. FIG. 4 shows the prosthetic device 50 attached to the mitral valve annulus 16. As shown, the elongate element 52 disposed above and attached to the annulus 16, with the reference elements 54 extending radially inward toward a center of the valve annulus. As shown in FIG. 4, the reference elements 54 are disposed at or about the plane of the annulus 16. According to other embodiments, the reference elements 54 are disposed slightly above or slightly below the plane of the annulus 16.

Once the physician has attached the prosthetic device 50 to the annulus 16, the physician may connect neocords between the papillary muscles and the valve leaflet. During this procedure, the physician extends the neocord through the valve leaflet and ties the neocord onto the reference elements 54. Any excess portion of the neocord may then be cut off to leave a correct length for repair of prolapse of the leaflet or leaflets. The physician may then cut the reference elements 54 to free the neocords, which remain attached to the leaflet.

Figure 5:
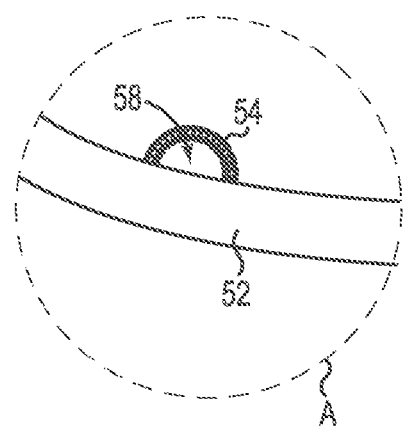
FIG. 5 is a close-up view of portion A of FIG. 3.

FIG. 5 shows an enlarged portion of the prosthetic device marked "A" in FIG. 3. Reference element 54 is shown including a needle-passing lumen 58. Reference element 54 in FIG. 5 is also shown as comprising a thread, or suture, coupled (e.g., fixed directly) to the elongate element 52. Other suitable configurations of reference elements 54 are contemplated that are able to then be cut or opened or otherwise removed in order to release knotted neocords having a desired length.

Figure 6:
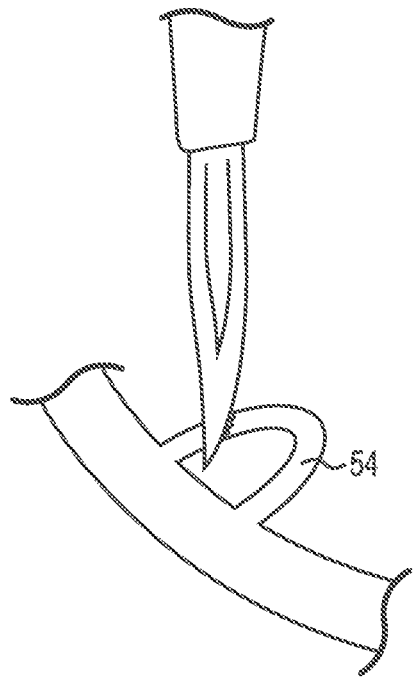
FIG. 6 is a close-up view of a reference element being cut according to an embodiment of the invention.

FIG. 6 shows an enlarged view of another embodiment of a reference element 54 being cut open. As shown, the physician may use a blade (e.g., scalpel or scissors) to cut or separate a portion of the reference element 54 to allow separation of a neocord tied to the reference element 54.

Figure 7:
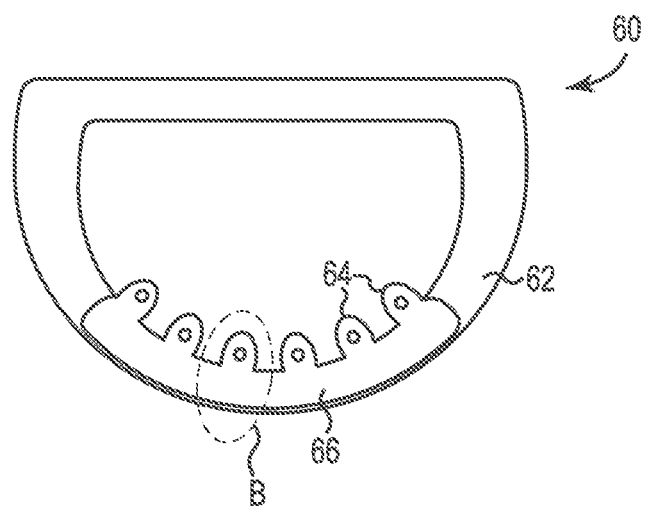
FIG. 7 is a plan view of a prosthetic device according to an embodiment of the invention.

FIG. 7 shows an exemplary embodiment of a prosthetic device 60 according to the invention. As shown, the prosthetic device 60 includes an elongate element 62 having a shape similar to a letter "D." According to various configurations, the prosthetic device 60 may have an open configuration and is generally shaped, for example, like a letter "C." According to other embodiments, the prosthetic device 60 has a closed configuration and is generally shaped, for example, like a letter "O" or a letter "D." According to various embodiments, the size and shape of prosthetic device 60 are selected to generally match the configuration of a patient's mitral valve annulus.

As shown in FIG. 7, a plurality of reference elements 64 are included on a strip 66 that is coupled to the elongate element 62. The strip 66 is releaseably coupled (e.g., by sutures) to the elongate element 62. During use, after attaching the neocords to the reference elements 64, the physician may separate the strip 66 and remove it from the elongate element 62. In various implementations, the physician my also cut each of the reference elements 64 to free the neocords from the strip 66.

Figure 8:
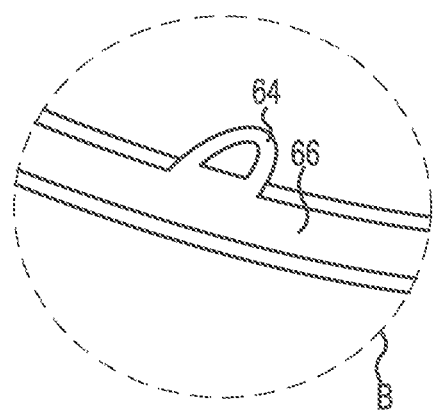
FIG. 8 is a close-up view of portion B of FIG. 7.

FIG. 8 shows a close-up of one reference element 64 from FIG. 7 (encircled portion marked "B" in FIG. 7). The close-up view shows that the reference element 64 is part of a strip 66 that is releasably attached to elongate element 62. The strip 66 may be made of any suitable material that may be easily removed from elongate element 62. The strip 66 may be attached to elongate element 62 by an adhesive material or any other suitable means, prior to its removal. According to other embodiments, the strip 66 is attached to the elongate element 62 in a non-releasable manner.

Figure 9A:
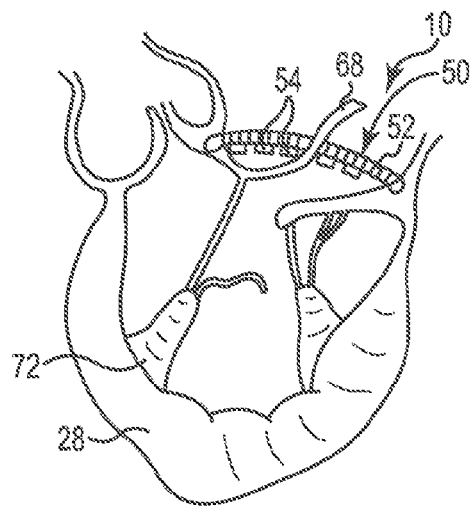
FIGS. 9A-9C are three schematic views showing steps in the application of a prosthetic device according to an embodiment of the invention.
Figure 9B:
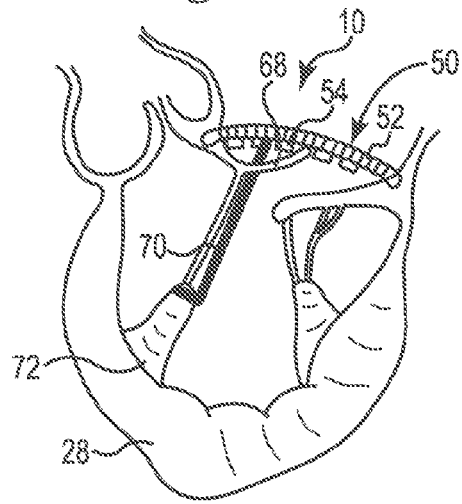
Figure 9C:
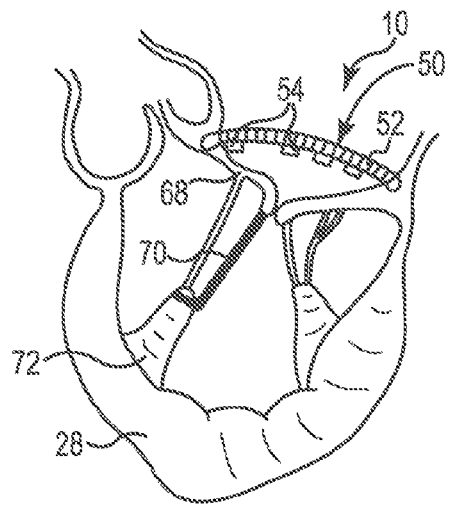

The use of a prosthetic device in accordance with the invention (e.g., the prosthetic device 50 shown in FIG. 3) is detailed below with reference to FIGS. 9A-9C, which provide schematic illustrations of steps in the use. As shown in FIG. 9A, a prolapsing segment 68 of a leaflet of mitral valve 10 is first identified. One end of a neocord 70 (FIG. 9B) is stitched to a fibrous head 72 of the papillary muscle 28, leaving the opposite end of the neocord 70 free. The physician then performs an annuloplasty of the posterior ring of the mitral valve 10, with the elongate element 52 of the prosthetic device 50 being anchored at its ends to the trigones. Next, the free end of the neocord 70 is then tied to (or knotted onto) one reference element 54, as shown in FIG. 9B. Any additional or excess length of the neocord 70 that extends beyond the knot may then be cut off. The reference element 54 is next cut open, freeing the knotted end of the neocord 70 from the elongate element 52.

According to various embodiments, the free end of the neocords 70 is simultaneously coupled (e.g., tied or knotted) to both the reference element 54 and the corresponding (e.g., prolapsing) segment 68 of the leaflet. In these embodiments, the physician then opens (e.g., by cutting with a scalpel) the reference element 54 such and frees the end of the neocord from the reference element 54, such that the neocords remains coupled to the leaflet.

Figure 10A:
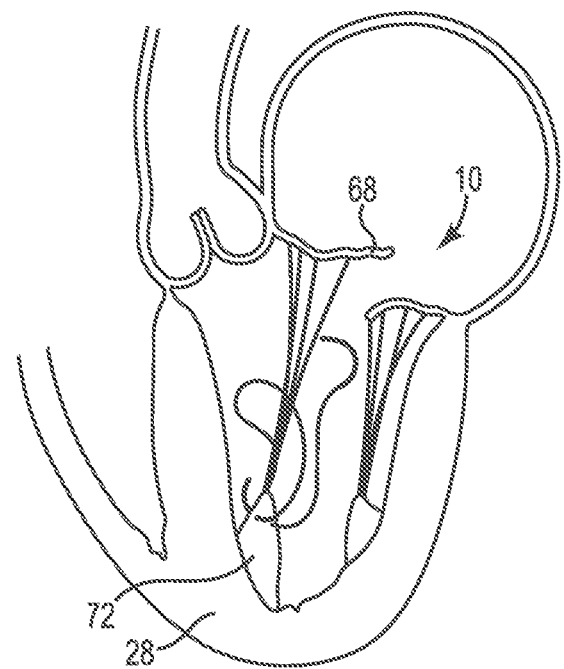
FIGS. 10A-10D are schematic views showing steps in the application of a prosthetic device according to another embodiment of the invention.
Figure 10B:
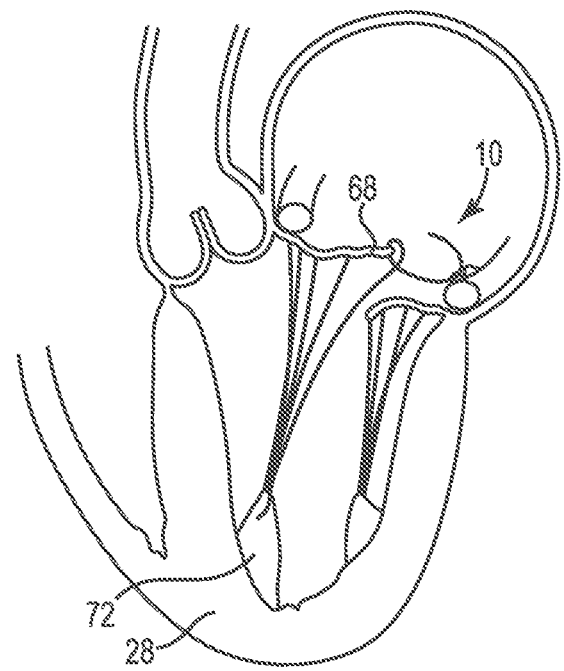
Figure 10C:
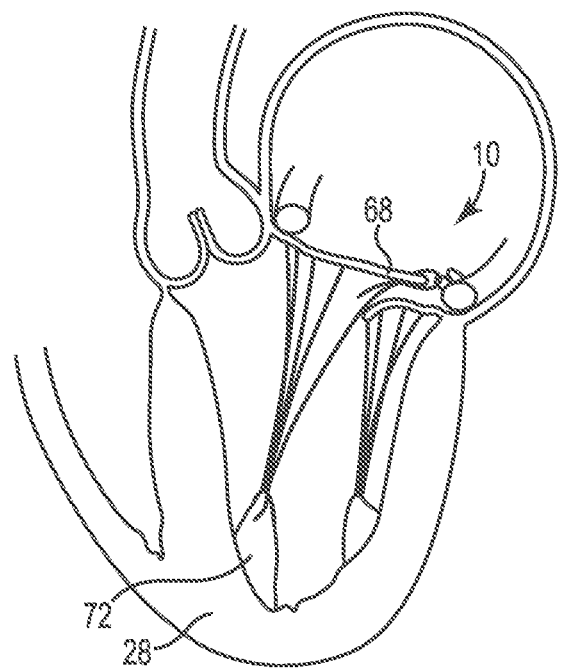

FIGS. 10A-10D illustrate an exemplary method of using the prosthetic device 50. As shown in FIG. 10A, a needle is used to attach a first end of a neocord 70 to a papillary muscle 72. Next, a needle is used to extend an opposite end of the neocords 70 through a prolapsed segment 68 of a leaflet of the mitral valve. As shown in FIG. 10B, the neocord 70 extends through the leaflet then through a reference element 54 of the prosthetic device 50. Next, as shown in FIG. 100, the neocords 70 is extended again through the proslapsed segment 68 of the leaflet. The end of the neocord 70 is then pulled to remove the slack from the neocord 70 between the papillary muscle 72 and the reference element 54. Next, the neocords 70 is knotted at or near the leaflet segment 68 to establish and fix and operable length (i.e., the distance from the papillary muscle 72 to the location of attachment to the leaflet segment 68) of the neocord 70.

Figure 10D:
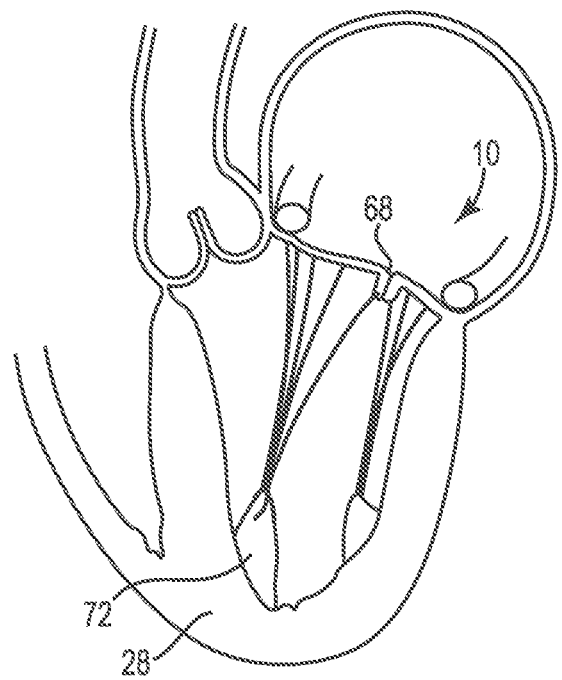

According to various embodiment, the process described above with reference to FIGS. 10A-100 is repeated for each desired neocords 70. The number and spacing of neocords 70 is determined by the physician, based on the nature of the prolapse present in a particular patient. Once the physician has completed the attachment process for the desired neocords 70 (or for the desired plurality of neocords 70), as shown in FIG. 10D, the neocords 70 are separated from the reference elements 54.

According to various embodiments wherein the reference elements 54 are formed by a thread, the physician pulls on the thread forming the reference elements. This pulling force removes the thread from the prosthetic device 50 and, during this process, the thread pulls through and thus separates from the knots formed in the neocords 70. In this way, each neocords 70 is separated from the reference element 54, but remains attached to the prolapsed segment 68. According to other exemplary embodiments, the reference element 54 is opened (e.g., cut) to allow the neocord 70 to exit from the reference element 54, which is then removed from the patient. In this way, the neocord 70 now extends between the papillary muscle and the prolapsed segment of the leaflet, with a length that has been determined using the prosthetic device 50.

Figure 11:
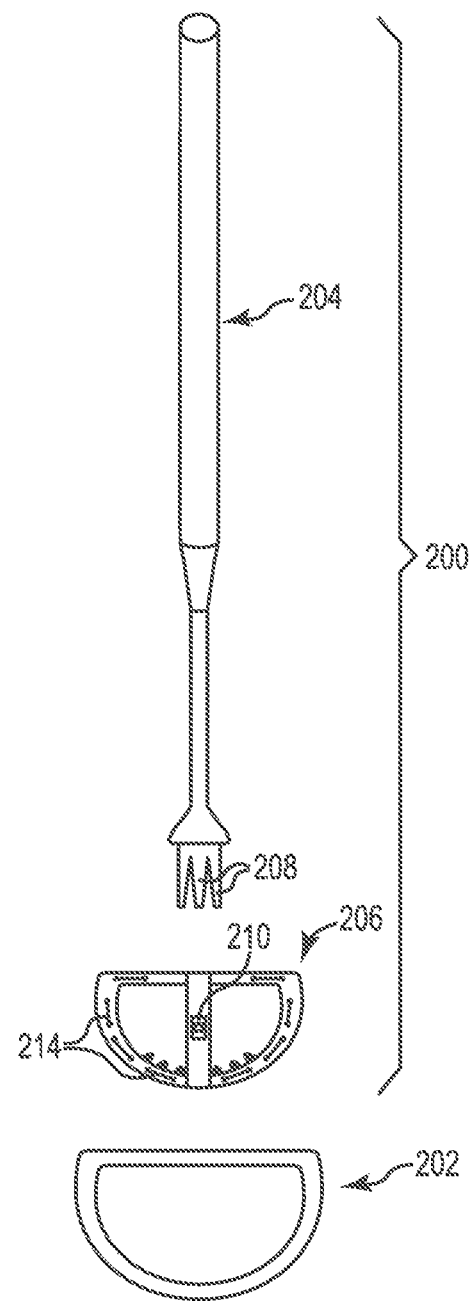
FIG. 11 is an exploded, perspective view of an annuloplasty ring in combination with a holder according to an embodiment of the invention.

Another embodiment of the invention is shown in FIG. 11. One embodiment of a holder 200 for use with an annuloplasty device 202 (for example) is illustrated in FIG. 11, and designated in its entirety by the reference numeral 200. The holder 200 comprises an elongate handle 204 and a retaining member (e.g., a plate or annular frame) 206. The retaining member 206 may, for example, be alternatively used to retain an annuloplasty device having an alternative shape. More generally, the retaining member 206 could be described as a holding member. The purpose of the holder 200 is to deliver and retain the annuloplasty device 202 at a mitral valve annulus during a implantation procedure.

The retaining member 206 is selectively mounted on the handle 204. The retaining member 206 of the holder 200 is adapted to retain the annuloplasty ring 202 shown during implantation of the annuloplasty ring 202. Thus, in accordance with the one embodiment, the general perimeter shape of the retaining member 206 corresponds generally with a shape of the mitral valve annulus. Alternatively, of course, a perimeter shape of the retaining member 206 can vary from that shown. According to various embodiments, the retaining member 206 is formed of transparent biocompatible thermoplastic or synthetic resin material, such as polycarbonate or polysulfone. The handle 204 may be of metal, such as an anodized aluminum alloy or stainless steel, or a suitable thermoplastic, thermoset or synthetic resin material.

The handle 204 of the holder 200 may be, for example, designed for a snap-fit engagement in the retaining member 206. The snap-fit engagement may be provided by a plurality of cantilever spring fingers 208 that are received in a slot 210 in the retaining member 206. This snap-fit mechanism allows the handle 204 to be attached to the retaining member 206 by surgical staff. Alternatively, any suitable temporary or permanent means for attaching the handle 204 and retaining member 206 may be employed.

Figure 12:
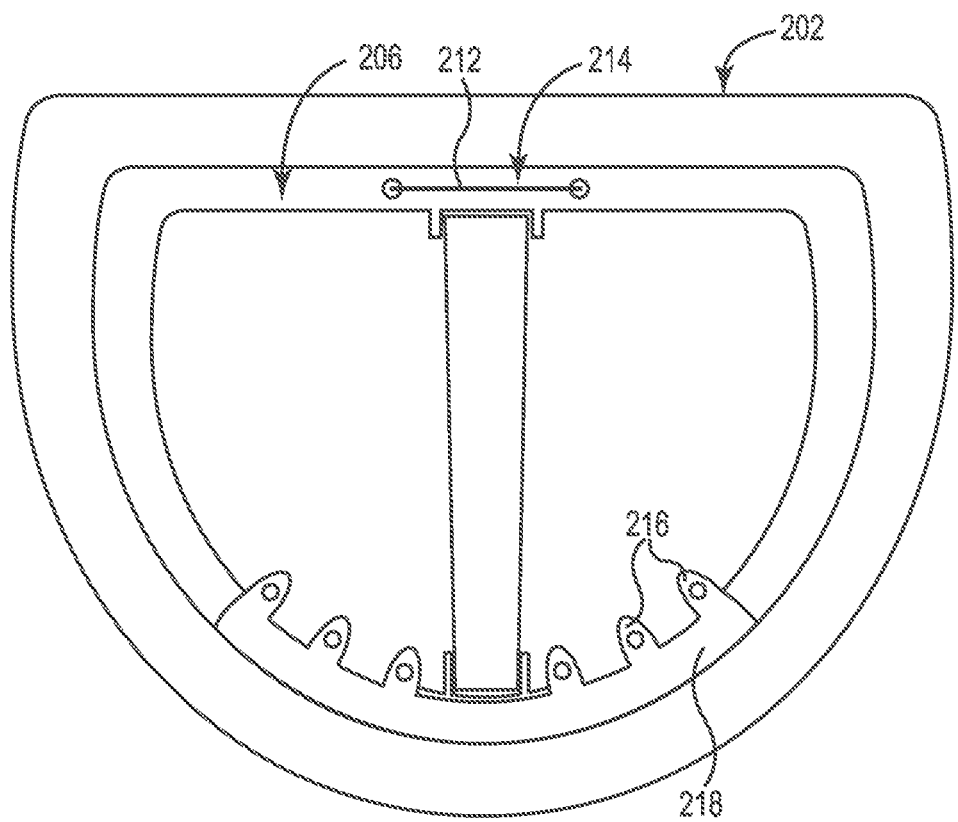
FIG. 12 is a bottom view of an assembled annuloplasty device and holder according to an embodiment of the invention.

According to various embodiments, the annuloplasty device 202 is mounted on the holder 200 at time of manufacture, and the assembly (or combination) is provided as a sterile unit. In one embodiment, and as illustrated in FIGS. 11 and 12, the retaining member 206 is adapted to receive a suture 212 in a plurality of spaced passage pairs 214 that are employed to secure the annuloplasty ring 202 to the retaining member 206. Each passage pair 214 includes two holes extending transversely through the retaining member 206. Each of the holes is adapted to allow passage of the suture 212. Further, as shown in FIG. 11, the holes comprising any one of the passage pairs 214 are separated by a section of the retaining member 206. In other words, each of the passage pairs 214 includes two distinct holes, and is not a continuous slot. With this configuration, the suture 212 can be threaded around, and thus engaged by, the retaining member 206 as shown in FIG. 11 and as also show in FIGS. 13A and 13B.

Figure 13A:
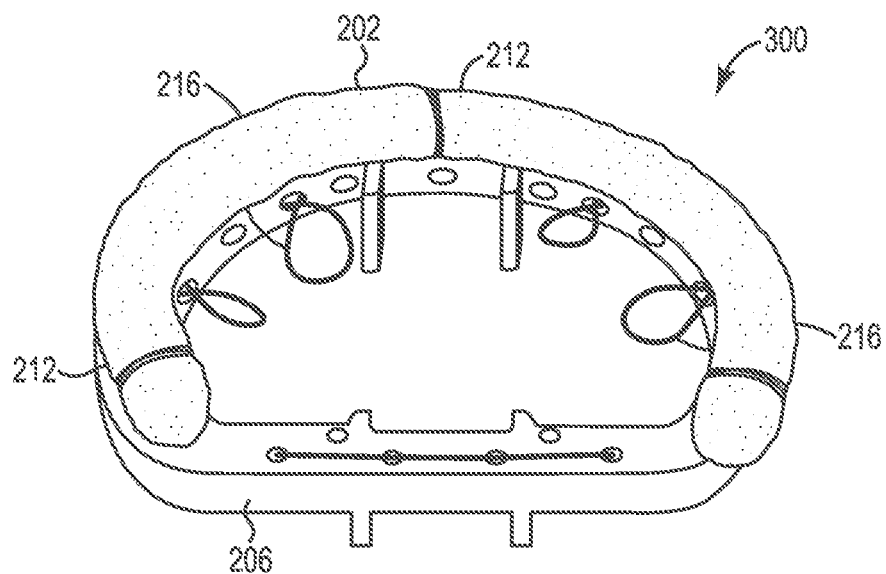
FIG. 13A is a bottom view and FIG. 13B is a top view of an assembled annuloplasty device and holder including suture loops according to an embodiment of the invention.
Figure 13B:
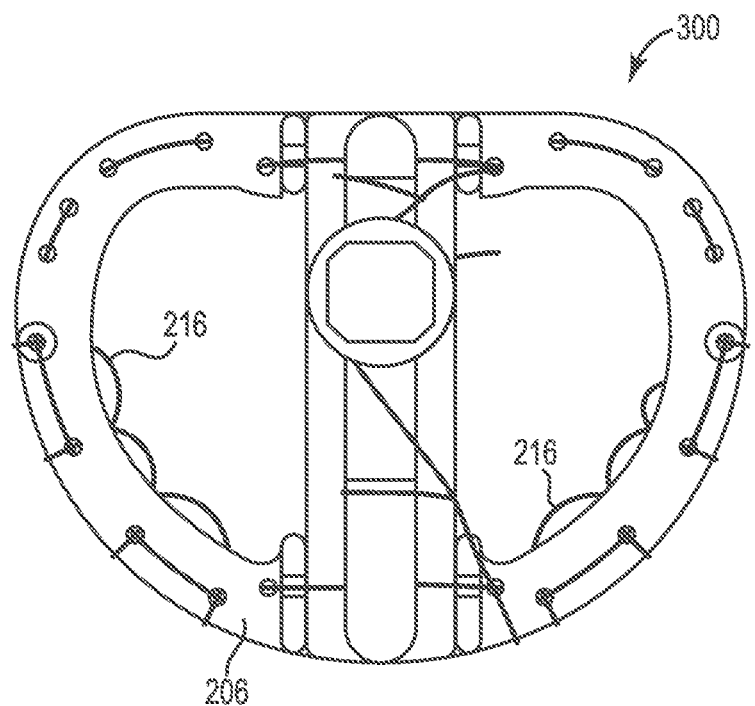

The above-described mounting technique is one of several known technique for securing the annuloplasty ring 202 to the retaining member 206. Alternative configurations/techniques can be employed for selectively mounting the annuloplasty device 202 to the retaining member 206. In some embodiments, if a suture is used, it is sewn to the annuloplasty device 202 at discrete and spaced apart positions from one another. Final assembly of the annuloplasty device 202 to the retaining member 206 is illustrated in FIGS. 13A and 13B. As depicted by the bottom view (FIG. 13A), the annuloplasty ring 202 is effectively mounted to a bottom surface of the retaining member 206.

As shown in FIGS. 12, reference elements 216 are associated with the retaining member 206. Such reference elements 216 may be separately attached to the retaining member 206 or may be part of an integrated strip 218 of reference elements 216 that is attached to the retaining member 206. The reference elements 216 are oriented toward the inner lumen of the annuloplasty device 202 and retaining member 206. Also, the reference elements 216 can have all the shapes and configuration as those described above with regard to other embodiments of the invention. In some embodiments, the reference elements 216 are coupled to a lower (i.e., closer to the valve annulus) surface of the retaining member, such that the reference elements are located at (or near) the plane of the annulus 10. In other embodiments, the reference elements 216 are coupled to an upper (i.e., further from the valve annulus) surface of the retaining member, such that the reference elements are located slightly above the plane of the annulus 10.

The holder 200 and annuloplasty ring 202 together may be directed to an implant site via maneuvering of the handle 204. Once at the implant site, the annuloplasty ring 202 is connected to the valve annulus with implanting sutures, which are placed, tightened, and tied. Before the holder 200 is removed, neocords are attached, at a first end, to a papillary muscle and, at a second end, to the reference elements 216 and to a corresponding portion of the leaflet. The reference elements 216 are then cut or removed. Next, the sutures 212 connecting the device 202 to the retaining member 206 are cut at the passage pairs 214, releasing the suture 212, and the holder 200 is removed.

FIGS. 13A and 13B show an alternative embodiment of an annuloplasty system 300 including an annuloplasty ring 202 coupled to a holder 206. As shown in FIG. 13A, the annuloplasty ring 202 is coupled to the holder 206 using a plurality of sutures 212 extending from the holder 206 circumferentially around the annuloplasty ring 202. As further shown in FIG. 13B, the holder 206 includes a plurality of loops 216 extending radially inwardly from the holder 206. While the embodiment of FIG. 13A includes four loops 216, other embodiments may include more or fewer loops 216. According to various embodiments, the loops 216 are disposed at circumferential locations corresponding to prolapsing segments of the native valve leaflets. According to other embodiments, however, the loops 216 may be disposed closer to the ring (and thus closer to the valve annulus) or the loops 216 may be disposed further from the ring (and thus further from the valve annulus). According to various embodiments, the loops have a diameter (and thus an extended length) sufficient to allow the loop to extend to a location at or near the valve annulus. According to various embodiments, the loops extend inwardly (e.g., away from an inner surface of the holder 206) a distance of from about 0.5 to about 4 mm. In various embodiments, the loops extend inwardly a distance of from about 1 to about 2 mm.

During use of the annuloplasty system 300, the physician may first position the annuloplasty holder 206 and ring 202 at a location adjacent an upper (i.e., outflow or atrial) portion of the valve annulus. The physician then sutures the ring 202 to the valve annulus. In addition, the physician attaches one or more neocords between an appropriate papillary muscle and a loop 216. According to various embodiments, the attachment to the loop 216 is made with a simultaneous attachment to a prolapsing segment of the mitral valve leaflet, such as for example by passing the neocords through the leaflet then tying or knotting an end of the neocords to the loop 216. During this process, the neocords may be attached with a small amount of tension, such that the loop 216 is caused to take an extended configuration. In this fashion, the diameter (or length) of the loop 216 determines the level at which the prolapsing segment of the leaflet will be allowed (by the neocords) to extend. Upon attaching the neocords to the loop (and the corresponding portion of the leaflet), the loop is cut or removed and the neocords remains attached to the leaflet. According to various embodiments, the holder and loop are then removed together.

Various modifications and additions can be made to the exemplary embodiments discussed without departing from the scope of the invention. Accordingly, the scope of the invention is intended to embrace all such alternatives, modifications, and variations as fall within the scope of the claims, together with all equivalents thereof.

We claim:

1. A prosthetic device for repairing a mitral valve having an annulus, leaflets, and chordae tendinae, the device comprising:
    an elongate element including a plurality of reference elements that are located along the elongate element and configured to protrude inwardly with respect to the elongate element towards a center of the annulus, the plurality of reference elements formed by attaching a single suture to the elongate element, wherein the single suture is attached to a plurality of locations on the elongate element to form the plurality of reference elements and the single suture is configured to receive a corresponding plurality of artificial cords that are tied onto the plurality of reference elements, wherein the plurality of reference elements are configured to be removed by cutting or removing the single suture to release the corresponding plurality of artificial cords that are tied onto the plurality of reference elements.

2. The prosthetic device of claim 1 wherein the elongate element is made of a flexible material.

3. The prosthetic device of claim 1 wherein the elongate element is arcuate in shape and has two free ends that are separated by an opening.

4. The prosthetic device of claim 1 wherein the elongate element is a closed ring.

5. The prosthetic device of claim 1 wherein the elongate element comprises a central core of a silicone material and an exterior covering of a polyester material.

6. The prosthetic device of claim 1 wherein each of the plurality of reference elements includes one needle-passing lumen.

7. A prosthetic device for repairing a mitral valve having an annulus, the prosthetic device comprising:
    an elongate element configured to be attached to the annulus and including a plurality of reference elements formed by attaching a single suture to the elongate element, wherein the single suture is attached to a plurality of locations on the elongate element to form the plurality of reference elements and the single suture is configured to receive one or more artificial cords that are tied to one or more of the plurality of reference elements, wherein the plurality of reference elements are configured to be removed by cutting or removing the single suture to release the one or more artificial cords that are tied to the one or more of the plurality of reference elements.

8. The prosthetic device of claim 7 wherein the elongate element is made of a flexible material.

9. The prosthetic device of claim 7 wherein the elongate element is arcuate in shape and has two free ends that are separated by an opening.

10. The prosthetic device of claim 7 wherein the elongate element is a closed ring.

11. The prosthetic device of claim 7 wherein the elongate element comprises a central core of a silicone material and an exterior covering of a polyester material.

12. The prosthetic device of claim 7 wherein each of the plurality of reference elements includes one needle-passing lumen.

\* \* \* \* \*